United States Patent
Abbestam et al.

(10) Patent No.: US 8,701,863 B2
(45) Date of Patent: Apr. 22, 2014

(54) DIVERTER DISC

(75) Inventors: Göran Abbestam, Partille (SE); Klas Ålander, Goteborg (SE)

(73) Assignee: FlexLink Components AB (SE)

( * ) Notice: Subject to any disclaimer, the term of this patent is extended or adjusted under 35 U.S.C. 154(b) by 0 days.

(21) Appl. No.: 13/988,221

(22) PCT Filed: Nov. 24, 2011

(86) PCT No.: PCT/SE2011/051422
§ 371 (c)(1),
(2), (4) Date: May 17, 2013

(87) PCT Pub. No.: WO2012/071008
PCT Pub. Date: May 31, 2012

(65) Prior Publication Data
US 2013/0240324 A1    Sep. 19, 2013

(30) Foreign Application Priority Data
Nov. 26, 2010 (SE) ..................... 1051242

(51) Int. Cl.
B65G 47/46 (2006.01)

(52) U.S. Cl.
USPC .................. 198/370.01; 198/457.07

(58) Field of Classification Search
USPC .............. 198/370.1, 430, 459.2, 457.02
See application file for complete search history.

(56) References Cited

U.S. PATENT DOCUMENTS

| | | | | |
|---|---|---|---|---|
| 2,358,315 A | * | 9/1944 | Campbell | 198/479.1 |
| 3,613,885 A | | 10/1971 | Rehse et al. | |
| 3,710,937 A | * | 1/1973 | Cook | 198/370.1 |
| 3,994,117 A | * | 11/1976 | Kinney | 53/77 |
| 4,479,582 A | | 10/1984 | Ducloux | |
| 4,723,661 A | | 2/1988 | Hoppmann et al. | |
| 5,658,532 A | * | 8/1997 | Kurosaki et al. | 422/64 |
| 5,853,077 A | * | 12/1998 | Schmitt | 198/383 |
| 6,168,004 B1 | * | 1/2001 | Drewitz et al. | 198/370.1 |

(Continued)

FOREIGN PATENT DOCUMENTS

| | | |
|---|---|---|
| DE | 2644137 A1 | 4/1978 |
| DE | 4329078 A1 | 3/1995 |
| WO | WO-2011/028166 A1 | 3/2011 |
| WO | WO-2012/071008 A1 | 5/2012 |

OTHER PUBLICATIONS

"International Application Serial No. PCT/SE2011/051422, International Search Report mailed Mar. 6, 2012", 4 pgs.

(Continued)

Primary Examiner — James R Bidwell
(74) Attorney, Agent, or Firm — Schwegman Lundberg & Woessner, P.A.

(57) ABSTRACT

Diverter disc for a conveyer system, comprising a circular outer periphery and an grip opening formed in the periphery of the diverter disc, where the grip opening is adapted to hold and divert a puck comprising a circular slide ring at the contact region and that the grip opening is shaped in a non circular shape such that a plurality of discrete contact points are formed in the grip opening. The advantage of the diverter disc is that it will be able to hold the slide ring of a puck in a more secure way due to the reduced contact surface compared with a conventional diverter disc.

8 Claims, 4 Drawing Sheets

(56) References Cited

U.S. PATENT DOCUMENTS

| | | | |
|---|---|---|---|
| 6,520,313 B1 | 2/2003 | Kaarakainen et al. | |
| 7,036,655 B2 * | 5/2006 | Schafer | 198/459.2 |
| 7,913,518 B2 * | 3/2011 | Winkelhake et al. | 198/370.1 |
| 2012/0228094 A1 * | 9/2012 | Ohman | 198/867.01 |

OTHER PUBLICATIONS

"International Application Serial No. PCT/SE2011/051422, International Preliminary Report on Patentability dated May 28, 2013", 6 pgs.

"International Application Serial No. PCT/SE2011/051422, Written Opinion mailed Mar. 6, 2012", 5 pgs.

* cited by examiner

DIVERTER DISC

RELATED APPLICATIONS

This application is a US National Stage application filed under 35 U.S.C. §371 from International Application Serial No. PCT/SE2011/051422, filed Nov. 24, 2011 and published as WO 2012/071008 A1 on May 31, 2012, which claims the priority benefit of Sweden Patent Application No.: 1051242-4, filed on Nov. 26, 2010, the contents of which applications and publication are incorporated herein by reference in their entirety.

TECHNICAL FIELD

The present invention relates to a diverter disc having an opening adapted for a carrier puck comprising a slide ring. The diverter disc is adapted to be used in a conveyor system.

BACKGROUND ART

Conveying devices, such as those which are used for moving objects between different stations in a factory, usually comprise a conveying track in the form of a belt or a chain. The conveying tracks can be recessed in a trench with vertical side surfaces. Alternatively, they can be located on the horizontal upper surfaces of the trench or arranged in some other way. The objects to be conveyed are arranged slidably in relation to the conveying tracks, either directly or via supporting means. Larger objects are often conveyed on supporting means also known as pallets, and smaller objects may be conveyed using a small carrier often referred to as a carrier puck.

A supporting means is conveyed along the conveying track, which may comprise different work stations. The work stations may be positioned along the conveying track such that all objects will pass all work stations. In this way, all objects must stop at the same time, regardless if an object is to be manipulated at a work station or not. Such an arrangement is not very flexible and is mostly used when all objects are to be manipulated in the same manner, and when the manipulation requires only a short time duration.

In more flexible systems, where different work stations can perform different operations on different objects, the work stations are separated from the main conveyor track. In such a system, each object can be directed to any work station without disturbing the flow on the main conveyor track. The duration of an operation at a work station will thus not affect the other objects. An object is directed into a side track by a diverting station. In order to be able to divert an object into a side track, the diverting station must be able to catch the right object from the main object flow and to move it out of the flow. If there are many objects travelling next to each other in the main flow, bearing on each other, the force required to move the puck out of the flow will be relatively high.

In some systems, a circular diverter disc having one or more grip openings is used to divert the pucks from the main conveyor track. In such systems, the pucks are circular such that they can be gripped by the diverter disc. The opening in the diverter disc is semi-circular and corresponds to the size and shape of the puck.

When a diverter disc grips the puck and moves it out of the main flow, the puck will be subjected to a rotational movement since the diverter disc rotates. The puck may rotate during the diversion but will most likely not rotate in relation to the diverter disc. With several other pucks bearing on the first puck, the diverter disc will have to overcome the force from the rest of the pucks that are pushed towards the first puck by the conveyor. This will lead to either that the first puck glides with a friction against the other pucks or that all the other pucks will be rotated by the first puck, or a combination of both. When a puck rotates, it will rub against the conveyor rails and possible against the neighbouring pucks. In either case, a relatively high force must be exerted by the diverter disc due to the friction between the pucks and the force applied on the pucks by the conveyor track in the direction towards the first puck.

One way of solving this problem is to introduce an extra stop function before the diverter station. The stop will interrupt the main flow such that a single puck can easily be directed out from the main conveyor track. Each stop is however an unnecessary cost and it also requires additional space.

Another possibility is to use a motor that is strong enough to overcome the force from the pucks in the main flow. When other pucks bear on the first puck, the diverter disc must overcome the force from all other pucks during the diversion. This requires a relatively large drive unit. In a large system having several work stations, the total power requirement will thus be unnecessarily high. When a first puck is diverted out of the main flow by a diverter disc, the diverter disc must apply a rotational torque that can overcome the force of the puck train acting on the first puck, either by rotating the pucks in the puck train, by sliding the first puck against the puck train or by sliding the first puck in the diverter disc.

DE 4329078 A1 describes such a diverter disc that is used to divert circular pucks by catching one puck at the time and to divert it in another direction. The remaining pucks will bear against the circumference of the disc.

U.S. Pat. No. 4,723,661 A also describes a similar diverter discs where a circular puck is diverted by the diverter disc and where the remaining pucks bear against the circumference of the disc.

U.S. Pat. No. 6,520,313 B1 describes a system in which such a diverter disc is used to divert circular pucks.

In all those documents, the puck is held by the semi-circular opening in the diverter disc. In order to obtain a low friction between the opening and the puck, the disc opening corresponds to the shape and size of the puck. This will minimize wear due to sliding between the disc opening surface and the outer puck surface.

These solutions work fine in some systems, but are anyhow subjected to the above mentioned problem. There is thus still room for improvements.

DISCLOSURE OF INVENTION

An object of the invention is therefore to provide an improved diverter disc that is adapted to divert pucks having a slide ring.

In a diverter disc for a conveyer system, comprising a circular outer periphery and an grip opening formed in the periphery of the diverter disc, the object of the invention is achieved in that the grip opening is adapted to hold and divert a puck comprising a circular slide ring at the contact region and that the grip opening is shaped in a non circular shape such that a plurality of discrete contact points are formed in the grip opening.

By this first embodiment of the diverter disc according to the invention, the diverter disc is able to hold the slide ring of a puck in a firm grip during the diversion of the puck. This is achieved in that the discrete contact points exhibit a relatively small contact surface, which in turn will provide a relatively high contact pressure between the slide ring and the discrete contact points. The slide ring can rotate freely on the puck and is adapted to let the puck rotate relative the slide ring when the puck is diverted by a diverter disc. Because the diverter disc will grip the puck at the slide ring, the diversion will not require as much power as when conventional pucks are diverted by a conventional diverter disc, since the diverter disc and the puck will be able to move relative each other. This will improve the performance of the system.

In an advantageous development of the invention, the grip opening is provided with protrusions which will decrease the contact surface further.

This will improve the performance of the system further, since the contact pressure between the slide ring of a puck and the discrete contact points of the grip opening will be increased.

In an advantageous development of the invention, the base of the grip opening is further provided with a resilient means. The resilient means will constitute the inner contact point of the grip opening. The resilient means can be used for positioning purposes, when the puck is to be held in a fixed position in a positioning station.

BRIEF DESCRIPTION OF DRAWINGS

The invention will be described in greater detail in the following, with reference to the embodiments that are shown in the attached drawings, in which.

MODES FOR CARRYING OUT THE INVENTION

The embodiments of the invention with further developments described in the following are to be regarded only as examples and are in no way to limit the scope of the protection provided by the patent claims.

Figure 1:
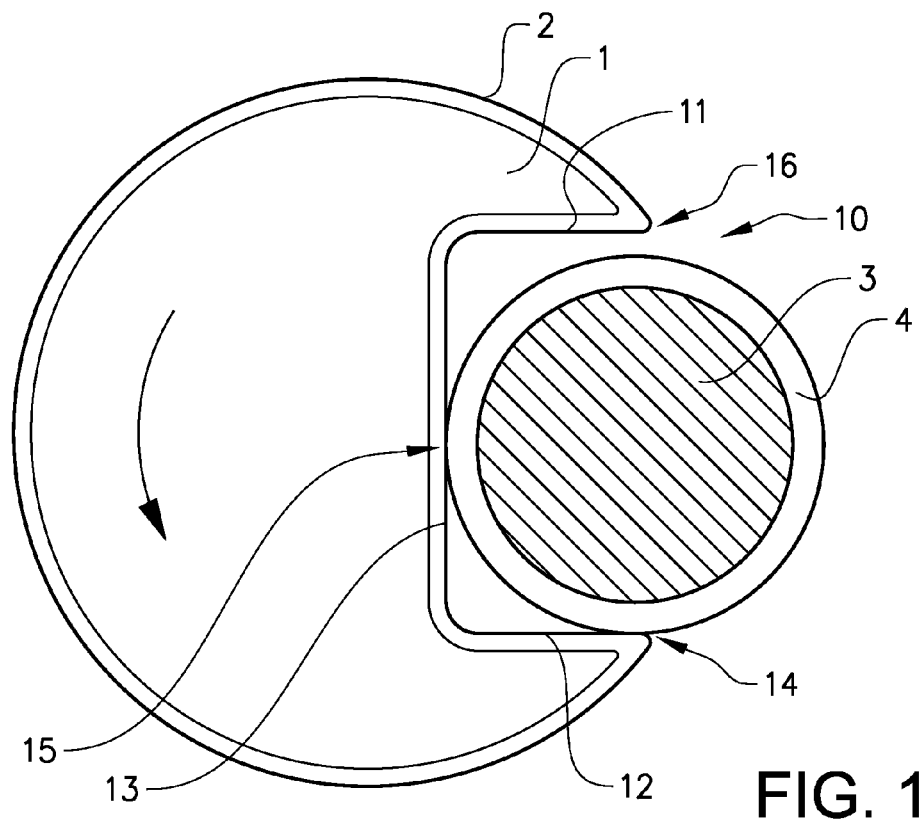
FIG. 1 shows a top view of a first embodiment of a diverter disc according to the invention.

FIG. 1 shows a first embodiment of a diverter disc according to the invention. The diverter disc is mainly adapted to be used with pucks having a slide ring in the contact region between the grip opening and the puck, where the diverter disc holds the puck. It is however also possible to use the diverter disc with conventional pucks, even though a conventional puck will not make use of the advantages of the inventive diverter disc. The diverter disc is adapted to be used in a conveyor system comprising a conveyor track on which the pucks are transported. The conveyor track may be either a chain conveyor or may comprise vertical, horizontal or round belts. The diverter disc is used to divert a puck from a first conveyor track into another conveyor track or to divert a puck from the conveyor track into a processing station of some kind. During the diversion of a puck, the remaining pucks of a puck train or queue of pucks will bear on the periphery 2 of the diverter disc.

The diverter disc 1 is mainly adapted to be used with pucks 3 having a slide ring 4 in the grip contact region. The grip opening is therefore provided with at least two discrete contact points against which the slide ring of the puck will bear when the puck is held by the opening. The discrete contact points may be achieved in different ways, depending on the system requirements of the complete conveyor system and on the type of processing stations used in the system. In the figures, a view of a puck 3 cut at the contact region is shown, such that the slide ring 4 is visible.

The advantage of the inventive diverter disc is that the contact pressure between the discrete contact points of the opening and the slide ring of the puck will be relatively high, in comparison to a conventional semi-circular opening having a shape that corresponds to the puck. This will assure that the slide ring is held in a fixed manner by the grip opening, such that the slide ring will not slide against the inner surface of the opening. Instead, it is ensured that the slide ring and the puck will rotate relatively each other when the puck is diverted by the diverter disc. This will reduce wear of the diverter disc and of the pucks. Further, this will reduce the power requirements of the drive motor of the diverter disc and will thus preserve energy. This allows for the use of a weaker drive motor than in conventional systems, which in turn will allow the diverter disc to be stopped by hand by an operator. This will eliminate the possibility of injury to the operator.

A conventional puck held by a conventional diverter disc may either be held in a fixed position by the opening or may slide against the inner surface of the opening. This will depend e.g. on the type of conveyor track, on the type of the pucks used and on the amount of pucks that queue up at a diverter station. A conventional puck and semi-circular opening combination is thus made to correspond to each other in order to reduce the wear between the puck and the opening.

The grip opening of the inventive diverter disc is further wider than the diameter of the puck. The distance between the two outer contact points of the opening is thus at least 1.05 times the diameter of the slide ring of the puck. In this way, it is ensured that the puck can enter the opening freely and that only two contact points will bear on the slide ring during a diversion of the puck. This will further increase the contact pressure between the discrete contact points and the slide ring.

FIG. 1 shows a first embodiment of an inventive diverter disc. This opening is made with a square shape, having two parallel side walls and an inner wall being perpendicular to the side walls. Such an opening will reduce the contact surface between the slide ring and the grip opening. The grip opening 10 of the diverter disc 1 is provided with a first side wall 11, a second side wall 12 and an inner wall 13. This shape of the grip opening will in combination with a slide ring 4 of a puck provide three discrete contact points 14, 15 and 16. A puck 3 having a slide ring 4 is shown in the grip opening. In the shown example, the diverter disc is rotated in a counter-clockwise direction indicated by an arrow. The slide ring will thus bear only on the discrete contact points 14 and 15 during the diversion.

Figure 2:
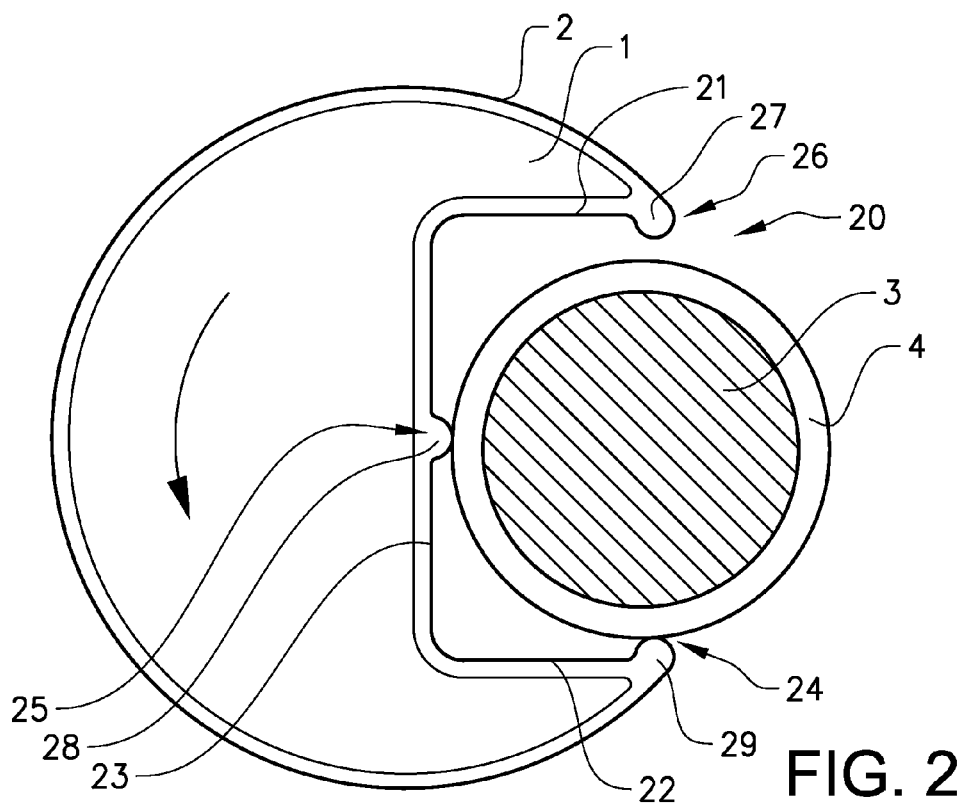
FIG. 2 shows a development of the first embodiment of a diverter disc according to the invention.

In a development of the first embodiment, shown in FIG. 2, the contact surface is reduced further by introducing protrusions that extend from the side walls and the inner wall of the grip opening, forming discrete contact points. The grip opening 20 of the diverter disc 1 is in this example provided with a first protrusion 27 on the first side wall 21, a second protrusion 29 on the second side wall 22 and an inner protrusion 28 on the inner wall 23. This shape of the grip opening will in combination with a slide ring 4 of a puck provide three contact points 24, 25 and 26. A puck 3 having a slide ring 4 is shown in the grip opening. In the shown example, the diverter disc is rotated in a counter-clockwise direction indicated by an arrow. The slide ring will thus bear only on the discrete contact points 24 and 25 during the diversion. By using protrusions to form the contact points, the contact surface will be reduced further. Such a solution will ensure that the slide ring is held in a fixed manner by the grip opening during a diversion of the puck.

It is further possible to apply a friction material on one or more of the contact points, e.g. on one or more of the protrusions in order to reduce the risk of slippage further. A suitable friction material may be e.g. rubber or plastic. In one example, the inner protrusion 28 is provided with a friction material. In this way, the slide ring can still slide against one of the outer discrete contact points 26, 27 when entering or leaving the opening. In another example, the two outer protrusions are provided with a friction material. In this way, the slide ring will pivot around the contact point when entering or leaving the grip opening. In both cases, the contact ring will be firmly held during a diversion.

Figure 3:
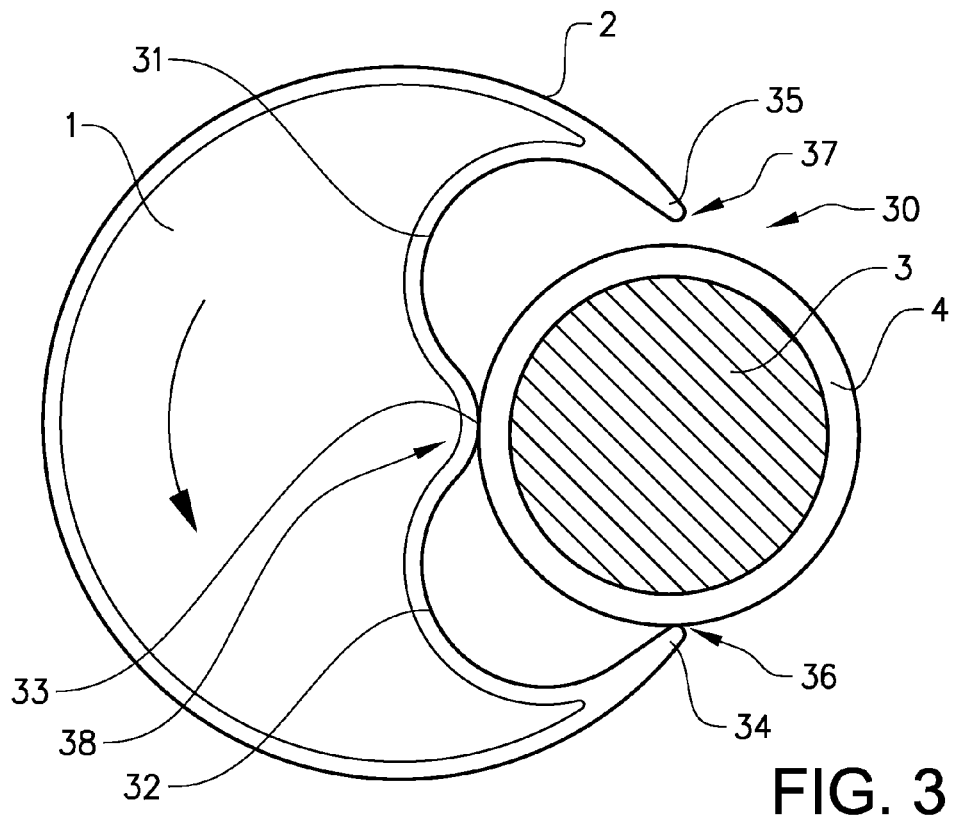
FIG. 3 shows a further example of a diverter disc according to the invention.

A further example of a diverter disc having three discrete contact points is shown in FIG. 3. In this example, the grip opening comprises two semi-circular cut-outs 31, 32 with a common centre portion 33, where the centre portion will constitute the inner contact point 38. The periphery 2 of the diverter disc 1 and the first semi-circular cut-out 31 are delimited by an extending first outer projecting nose 34. A second outer projecting nose 35 is formed in the same way. The first projecting nose 34 will constitute a first outer contact point 36 and the second projecting nose 35 will constitute a second outer contact point 37. A diverter disc with such a grip opening can be used both for a puck having a slide ring and for a puck having a non-cylindrical contact region, e.g. having one or more indentations in the contact region. An indentation is formed to correspond to the centre portion 33. Such a puck can be held in a fixed orientation in the grip opening with an indentation resting on the centre portion. A puck 3 having a slide ring 4 is shown in the grip opening. In the shown example, the diverter disc is rotated in a counter-clockwise direction indicated by an arrow. The slide ring will thus bear only on the discrete contact points 36 and 38 during the diversion.

Figure 4:
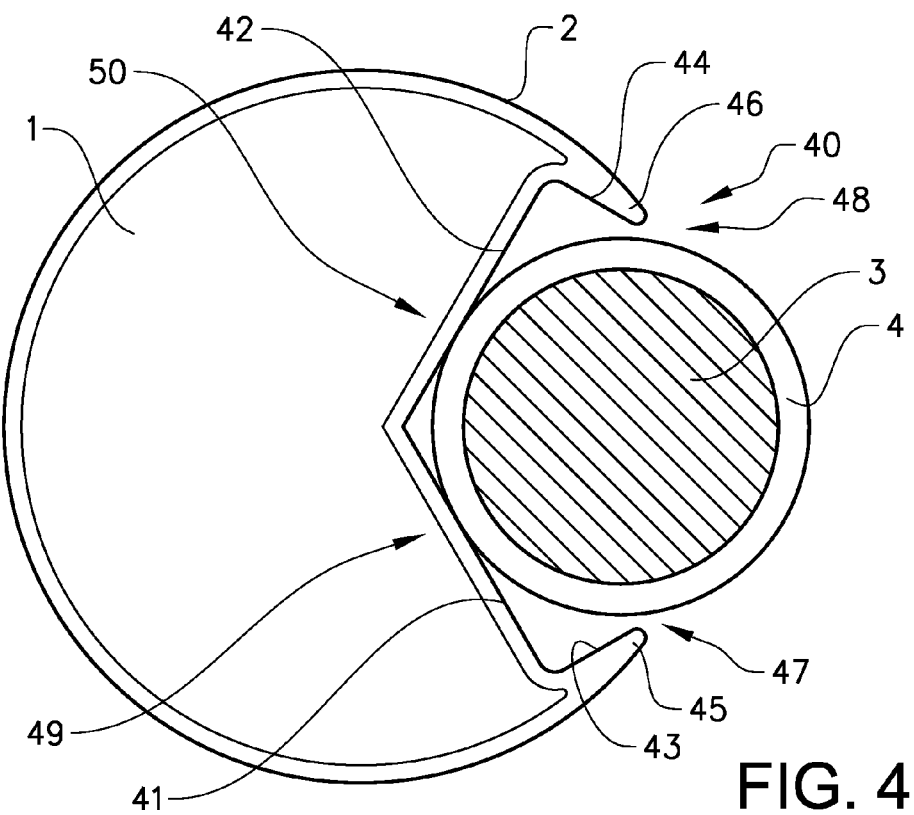
FIG. 4 shows a further example of a diverter disc according to the invention.

FIG. 4 shows a further example of a diverter disc. The grip opening 40 comprises in this example a V-shaped base consisting of a first inner wall 41 and a second inner wall 42. The opening further comprises two side walls 43, 44. The side walls are in the shown example angled with respect to each other, but they may also be parallel. The side walls ends in projecting noses 45, 46. The projecting nose 45 will constitute a first outer contact point 47 and the projecting nose 46 will constitute a second outer contact point 48. The V-shaped grip opening base will centre the puck when the diverter disc is standing still. This may be of advantage if the puck is to be held in a fixed position in a work station, where the puck is resting against a resilient member of the work station. The position of the puck is thus defined by the grip opening of the diverter disc. The precision of such a fixed position may be high enough for some types of operations.

In the centred position, the puck will bear against two contact points of the inner walls. The example in FIG. 4 is shown in a non-rotating state. When the diverter disc rotates, the puck will bear against one of the contact points 49, 50 on one of the inner walls and either the contact point 47 or 48, depending on the direction of rotation. The contact pressure between the slide ring and the contact points will thus be relatively high.

Figure 5:
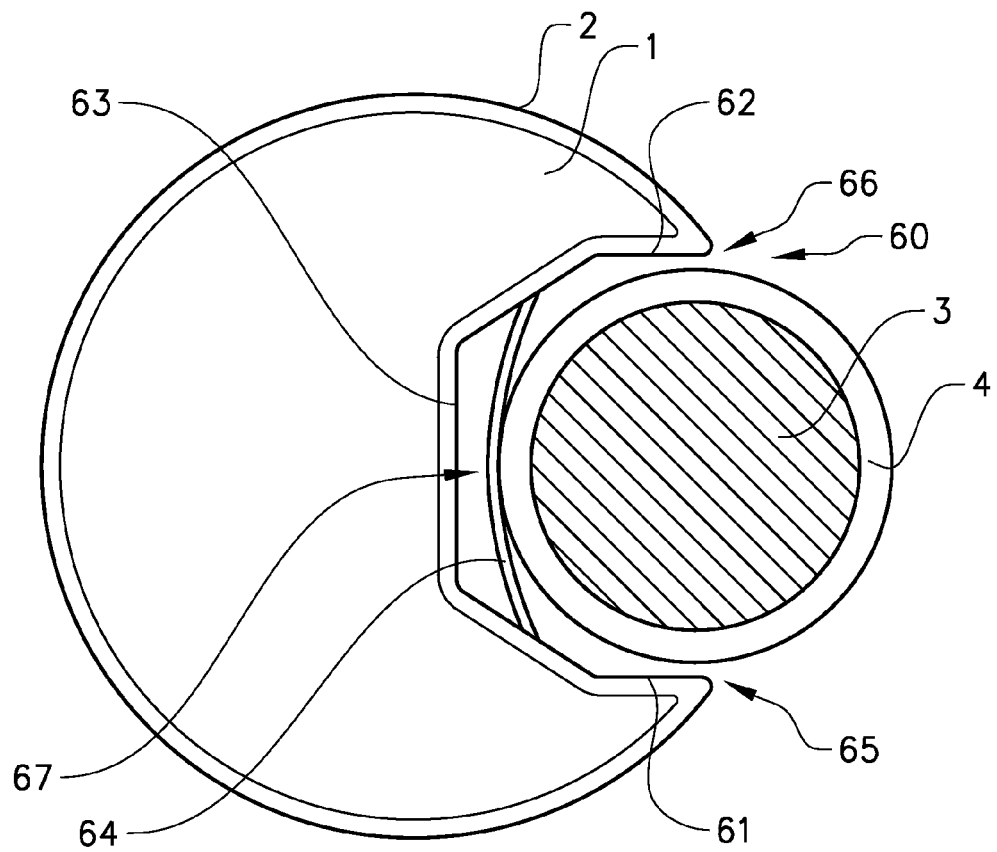
FIG. 5 shows a further example of a diverter disc according to the invention.

In another example, the inner contact point in the disc opening is replaced with a resilient means. In FIG. 5, an example of a grip opening comprising a blade spring is shown. The opening 60 comprises two parallel side walls 61, 62 which may extend directly to the base wall 63 or may comprise an intermediate angled wall portion. A resilient means, in the shown example a blade spring 64, is provided in the side walls. Other spring means may also be used, e.g. a coil spring suspended between the inner walls or a rubber or plastic spring provided on the base wall. The blade spring extends over the width of the opening and makes up the inner contact point for the slide ring of the puck. The blade spring may be formed with a slight concave shape or may be formed in an obtuse V-shape. The blade spring is primarily intended to be used when the diverter disc is used in a positioning station, which is adapted to hold the puck in a predefined fixed position. The positioning station thus comprises a position defining element, e.g. in the form of two sides of a V-shaped block, against which the puck will bear. The spring is adapted to push the puck towards the position defining element such that the puck will keep the predefined position during e.g. an operation. A predefined position having a high accuracy is thus obtained.

The spring will also provide a cushioning effect for a puck entering the grip opening. This may be an advantage when a puck train comprising several pucks reaches the diverter disc. When the diverter disc diverts a puck, the slide ring will bear on one of the outer contact points 65, 66 and a contact point 67 created between the blade spring and the slide ring. The slide ring will thus be supported by two contact points which will give a sufficiently high contact pressure to hold the slide ring in a firm grip.

A spring may be incorporated in any of the above exemplified and described grip openings.

The width of the grip opening, i.e. the distance between the two outer contact points, is preferably larger than the diameter of the slide ring by at least 5%. This will at one hand ensure that the puck can enter the grip opening without problems and on the other hand that the slide ring only bears against one of the outer contact points during a diversion of the puck.

The depth of the grip opening, i.e. the perpendicular distance from a line connecting the outer contact points and the inner contact point, is preferably approximately the same as the radius of the slide ring and is preferably in the range of 0.8 to 1.5 of the radius of the slide ring. With such a depth, the puck can enter and leave the grip opening in an easy way, and the puck can be diverted in a secure way. A deeper grip opening may obstruct the entering and leaving of the grip opening, a shallower grip opening may obstruct the diversion of a puck.

The material of the inner surface of the grip opening is dependent on the use of the diverter disc. If the diverter disc is to be used both with pucks having a slide ring and pucks without a slide ring, the material of the grip opening is preferably a low-friction material. For a grip opening that is only to be used with pucks having a slide ring, one or more of the contact points may be either of a low-friction material or of a friction material, depending on the use.

Figure 6A:
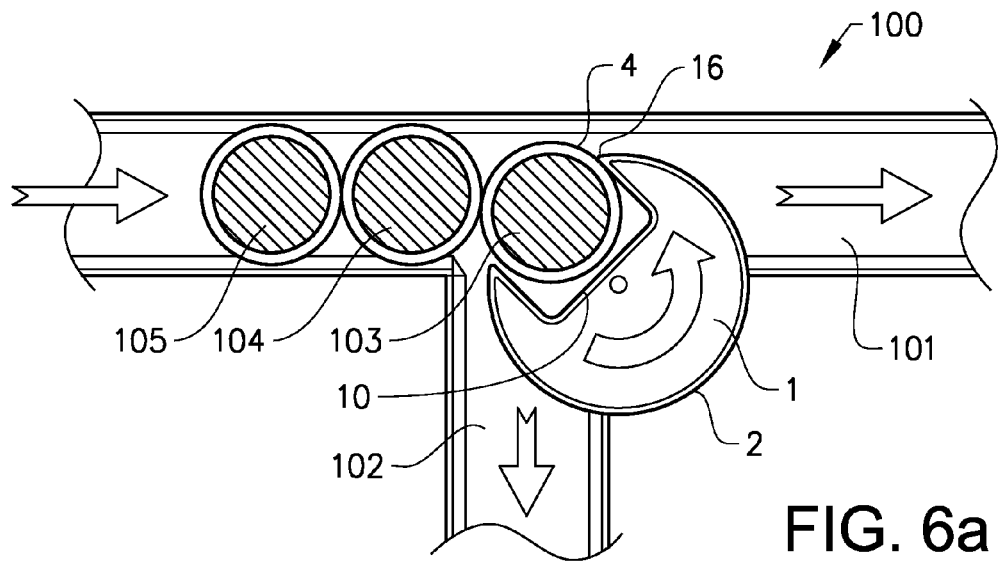
FIGS. 6a-6c show a puck being diverted in a conveyor system by a diverter disc according to the invention.
Figure 6B:
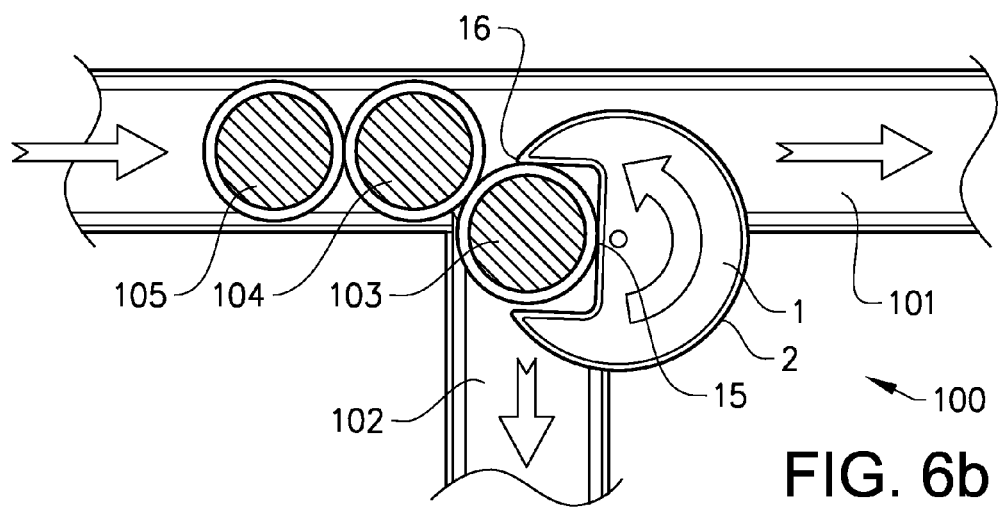
Figure 6C:
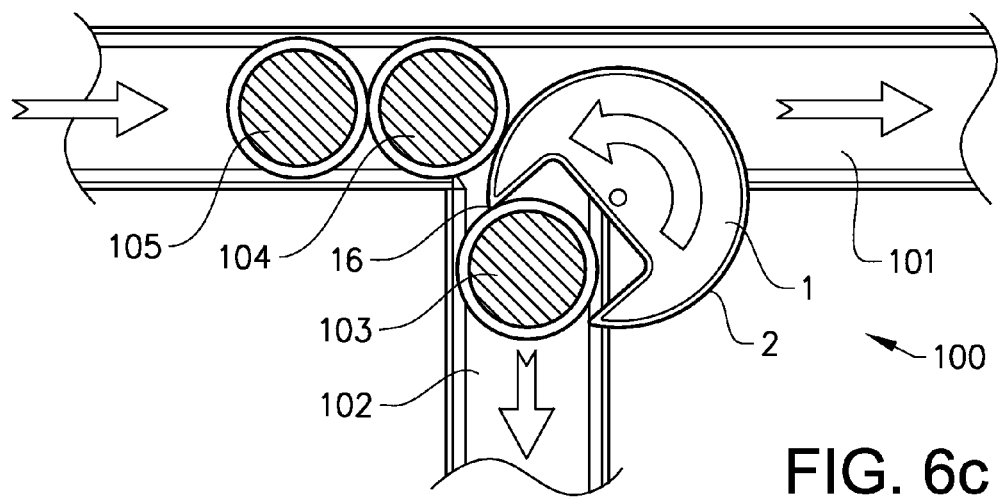

An example of a diversion of a puck having a slide ring using an inventive diverter disc is shown in FIGS. 6a to 6c. In this example, part of a conveyor system 100 is shown, in which a plurality of pucks are conveyed on a first conveyor track 101 and where a first puck 103 is to be diverted onto a second conveyor track 102 by a diverter disc 1. The diverter disc is in the shown example is exemplified with the diverter disc shown in FIG. 1. The travelling direction of the conveyor tracks are indicated with arrows. The diverter disc is provided with a grip opening 10 that is adapted to grip the slide ring 4 of the puck. In FIG. 6a, a first puck 103 has entered the grip opening of the diverter disc, which is in a first position. During the entering, the slide ring will bear on the contact point 16 and will pivot around contact point 16. The puck will rotate in the slide ring. A puck train with a leading second puck 104 bears on the first puck and is pushed against the first puck with a force that depends on the weight of each puck and the friction between the conveyor track and the puck train. Since the diameter of the slide ring is slightly smaller than the base of the puck, the bases of the pucks will bear on each other such that the slide rings of the pucks will not touch.

In FIG. 6b, the diverter disc rotates in a counter-clockwise direction indicated by an arrow. The puck will follow the diverter disc. Because of the slide ring, the puck will not be fixed to the diverter disc during this movement, but will be able to rotate relative the slide ring and the diverter disc. The puck will thus be able to roll against the second puck, during the diversion. In this way, the second puck and the other pucks in the puck train must not be rotated by the first puck, which is the case for a combination of a conventional diverter disc having a grip opening that corresponds to the shape of the puck and a conventional puck that is not provided with a slide ring. Since the pucks in the puck train do not have to be rotated, less force is required to rotate the diverter disc. There is also no need to introduce a puck stop in order to stop the puck train in order to relieve the first puck during the diversion. During the diversion, the slide ring bears on the two discrete contact points 15 and 16.

In FIG. 6c, the diverter disc has rotated to a second position where the first puck is diverted to the second conveyor track. When the first puck leaves the grip opening, the slide ring will bear on the contact point 16 and will pivot against this. After the puck has left the grip opening, the diverter disc can be rotated in a clockwise direction back to the first position in which it will catch the second puck which is next in turn. When the diverter disc rotates back to the first position, the periphery of the diverter disc will be in contact with the slide ring of the second puck. The slide ring of the second puck will thus rotate on the second puck, and the second puck will not rotate. When a conventional puck is used, either the pucks in the puck train must be rotated or the periphery of the diverter disc must slide against the puck. Rotating the puck train will require a relatively strong motor for the diverter disc, and sliding the periphery of the diverter disc against the puck will also require unnecessary power and will also induce wear on the surfaces.

When the second puck is caught by the diverter disc, the puck can either be diverted onto the second conveyor track by a counter-clockwise rotation or it can be forwarded on the first conveyor track by a clockwise rotation. When the puck is forwarded, the periphery of the diverter disc will cause the slide ring of the third puck 105 to rotate, which means that the third puck can keep its orientation and that less force is required.

The invention is not to be regarded as being limited to the embodiments described above, a number of additional variants and modifications being possible within the scope of the subsequent patent claims.

REFERENCE SIGNS

1: Diverter disc
2: Outer periphery
3: Puck
4: Slide ring
10: Grip opening
11: First side wall
12: Second side wall
13: Inner wall
14: Contact point
15: Contact point
16: Contact point
20: Grip opening
21: First side wall
22: Second side wall
23: Inner wall
24: Contact point
25: Contact point
26: Contact point
27: First protrusion
28: Inner protrusion
29: Second protrusion
30: Grip opening
31: Semi-circular cut-out
32: Semi-circular cut-out
33: Centre portion
34: First outer projecting nose
35: Second outer projecting nose
36: First outer contact point
37: Second outer contact point
38: Inner contact point
40: Grip opening
41: First inner wall
42: Second inner wall
43: Side wall
44: Side wall
45: Projecting nose
46: Projecting nose
47: First outer contact point
48: Second outer contact point
49: Contact point
50: Contact point
60: Grip opening
61: Side wall
62: Side wall
63: Base wall
64: Blade spring
65: Outer contact points
66: Outer contact points
67: Inner contact point
100: Conveyor system
101: First conveyor track
102: Second conveyor track
103: First puck
104: Second puck
105: Third puck

The invention claimed is:

1. A diverter disc for a conveyer system, comprising:
   a circular outer periphery and a grip opening formed in the periphery of the diverter disc,
   wherein the grip opening is adapted to hold and divert a puck comprising a circular slide ring at the contact region and that the grip opening is shaped in a non circular shape such that a plurality of discrete contact points are formed in the grip opening, wherein the grip opening comprises two parallel inner side walls.

2. The diverter disc according to claim 1, wherein at least one of the plurality of discrete contact points is provided with a friction material.

3. The diverter disc according to claim 1, wherein the plurality of discrete contact points includes a set of outer contact points that are arranged where the periphery of the diverter disc intersects with the inner walls of the grip opening.

4. The diverter disc according to claims 1, wherein the grip opening further comprises a resilient means arranged in the inner region of the grip opening, such that at least one inner contact point is provided on the resilient means.

5. The diverter disc according to claim 1, wherein the width of the grip opening is at least 5% larger than the diameter of the slide ring of the puck, which the diverter disc is adapted to divert.

6. A diverter disc for a conveyer system, comprising:
a circular outer periphery and a grip opening formed in the periphery of the diverter disc,
wherein the grip opening is adapted to hold and divert a puck comprising a circular slide ring at the contact region and that the grip opening is shaped in a non circular shape such that a plurality of discrete contact points are formed in the grip opening, wherein the grip opening,
wherein the grip opening comprises a plurality of protrusions that extend from an inner surface of the grip opening.

7. The diverter disc according to claim 6, wherein the grip opening comprises two semi-circular cut-outs.

8. A system comprising:
a conveyor system adapted to convey and divert pucks having a circular slide ring at the contact region between the grip region of a diverter disc and the puck, comprising at least one diverter disc further comprising:
a circular outer periphery an a grip opening formed in the periphery of the diverter disc, wherein the grip opening is adapted to hold and divert a puck comprising a circular slide ring at the contact region and that the grip opening is shaped in a non circular shape such that a plurality of discrete contact points are formed in the grip opening,
wherein the grip opening comprises two parallel inner side walls.

* * * * *

UNITED STATES PATENT AND TRADEMARK OFFICE
CERTIFICATE OF CORRECTION

PATENT NO. : 8,701,863 B2  Page 1 of 1
APPLICATION NO. : 13/988221
DATED : April 22, 2014
INVENTOR(S) : Abbestam et al.

It is certified that error appears in the above-identified patent and that said Letters Patent is hereby corrected as shown below:

Title page, item (57), in "Abstract", in column 2, line 2, delete "an" and insert --a--, therefor

Claims

In column 9, line 12-13, in Claim 6, after "opening,", delete "wherein the grip opening,", therefor In column 9, line 24, in Claim 8, delete "an" and insert --and--, therefor Signed and Sealed this
Sixth Day of October, 2015

Michelle K. Lee
*Director of the United States Patent and Trademark Office*